US011260055B2

(12) United States Patent
Shah et al.

(10) Patent No.: US 11,260,055 B2
(45) Date of Patent: Mar. 1, 2022

(54) ORAL PHARMACEUTICAL COMPOSITION OF LURASIDONE AND PREPARATION THEREOF

(71) Applicant: PIRAMAL PHARMA LIMITED, Mumbai (IN)

(72) Inventors: Tejas Shah, Ahmedabad (IN); Milan B. Agrawal, Ahmedabad (IN); Narendra Patel, Ahmedabad (IN); Devesh Bhatt, Ahmedabad (IN); Umesh Barabde, Ahmedabad (IN); Vipan Dhall, New Delhi (IN)

(73) Assignee: PIRAMAL ENTERPRISES LIMITED, Mumbai (IN)

( * ) Notice: Subject to any disclaimer, the term of this patent is extended or adjusted under 35 U.S.C. 154(b) by 0 days.

(21) Appl. No.: 16/476,385

(22) PCT Filed: Jan. 10, 2018

(86) PCT No.: PCT/IB2018/050142
§ 371 (c)(1),
(2) Date: Jul. 8, 2019

(87) PCT Pub. No.: WO2018/130943
PCT Pub. Date: Jul. 19, 2018

(65) Prior Publication Data
US 2020/0046695 A1 Feb. 13, 2020

(30) Foreign Application Priority Data
Jan. 11, 2017 (IN) .............................. 201721001137

(51) Int. Cl.
A61K 31/497 (2006.01)
A61K 9/00 (2006.01)
A61K 47/02 (2006.01)
A61K 47/26 (2006.01)
A61K 47/36 (2006.01)
A61K 47/38 (2006.01)

(52) U.S. Cl.
CPC .......... *A61K 31/497* (2013.01); *A61K 9/0053* (2013.01); *A61K 47/02* (2013.01);
(Continued)

(58) Field of Classification Search
CPC ...... A61K 31/497; A61K 31/496; A61P 25/28
See application file for complete search history.

(56) References Cited

U.S. PATENT DOCUMENTS 7,727,553 B2 6/2010 Fujihara
9,433,620 B2 9/2016 Khera et al.

FOREIGN PATENT DOCUMENTS

WO 2012/156981 A1 11/2012
WO 2014/068586 A2 5/2014
(Continued)

OTHER PUBLICATIONS

Sanford et al., CNS Drugs (2015) 29:253-263 (Year: 2015).*
(Continued)

Primary Examiner — San Ming R Hui
(74) Attorney, Agent, or Firm — Ladas & Parry LLP

(57) ABSTRACT

The present invention relates to an oral pharmaceutical composition, particularly a tablet, comprising an active ingredient lurasidone or its pharmaceutically acceptable salt(s) or solvate(s) thereof and one or more pharmaceutical excipient(s); and a process for its preparation.

15 Claims, 2 Drawing Sheets

(52) U.S. Cl.
CPC .............. *A61K 47/26* (2013.01); *A61K 47/36* (2013.01); *A61K 47/38* (2013.01)

(56) References Cited

FOREIGN PATENT DOCUMENTS

| | | |
|---|---|---|
| WO | 2014/076712 A2 | 5/2014 |
| WO | 2016/139683 A2 | 9/2016 |

OTHER PUBLICATIONS

International Search Report (ISR) for International Application No. PCT/IB2018/050142.
Written Opinion (WO) dated Jun. 1, 2017 for International Application No. PCT/IB2018/050142.
Frank Thielmann et al.; "The effect of primary particle surface energy on agglomeration rate in fluidised bed wet granulation" Powder Technology 181 (2008) 160-168.
Jonathan Bouffard et al.; "Influence of Process Variable and Physicochemical Properties on the Granulation Mechanism of Mannitol in a Fluid Bed Top Spray Granulator" Drug Development and Industrial Pharmacy, 31: 923-933, 2005.
Bhandari Neeraj et al.; "A review on immediate release drug delivery system" Int. Res. J. Pharm. App. Sci., 2014; 4(1):78-87.
Ranjith Reddy Kondeti et al.; "A Comparative Study on Different Methods of Granulation on Tablet Properties" Asian Journal of Pharmaceutical Technology and Innovation, vol. 2, No. 7 (2014), 1-5.

\* cited by examiner

ORAL PHARMACEUTICAL COMPOSITION OF LURASIDONE AND PREPARATION THEREOF

RELATED APPLICATION

This application is a national phase entry under 35 USC 371 of International Patent Application No.: PCT/IB2018/050142 filed on 10 Jan. 2018, which claims priority from Indian Application No. 201721001137 filed on 11 Jan. 2017, the disclosures of which are incorporated in their entirety by reference herein.

FIELD OF THE INVENTION

The present invention relates to an oral pharmaceutical composition comprising an active ingredient lurasidone or its pharmaceutically acceptable salt(s) or solvate(s) thereof and one or more pharmaceutical excipient(s). The invention further relates to a process for preparation of a pharmaceutical composition for oral administration, particularly a tablet, comprising lurasidone or its pharmaceutically acceptable salt(s) or solvate(s) thereof as an active ingredient along with one or more pharmaceutically acceptable excipient(s), wherein the composition is prepared by top spray granulation technique, which has a significant impact on drug release.

BACKGROUND OF THE INVENTION

Lurasidone hydrochloride is a psychotropic agent belonging to the chemical class of benzoisothiazole derivatives. Its chemical name is (3aR,4S,7R,7aS)-2-{(1R,2R)-2-[4-(1,2-benzisothiazol-3-yl)piperazin-1-ylmethyl]cyclohexylmethyl}hexahydro-4,7-methano-2H-isoindole-1,3-dione hydrochloride. Its molecular formula is $C_{28}H_{36}N_4O_2S \cdot HCl$ and its molecular weight is 529.14. The chemical structure is:

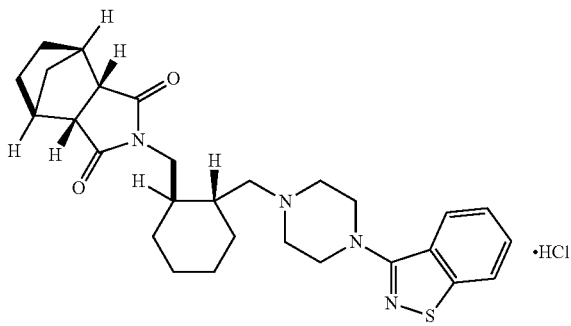

Lurasidone hydrochloride is a white to off-white powder. It is very slightly soluble in water, practically insoluble or insoluble in 0.1 N HCl, slightly soluble in ethanol, sparingly soluble in methanol, practically insoluble or insoluble in toluene and very slightly soluble in acetone.

LATUDA® tablets marketed in US and Europe are intended for oral administration only. Each tablet contains 40 mg or 80 mg of lurasidone hydrochloride. The inactive ingredients contained are mannitol, pregelatinized starch, croscarmellose sodium, hypromellose, magnesium stearate, Opadry® and carnauba wax. Additionally, the 80 mg tablet contains yellow ferric oxide and FD&C Blue No. 2 Aluminum Lake. LATUDA® is indicated for the treatment of patients with schizophrenia.

PCT Publication No. WO2014076712 provides a novel amorphous solid dispersion of lurasidone hydrochloride in combination with a pharmaceutically acceptable carrier, process for its preparation and pharmaceutical compositions comprising it.

U.S. Pat. No. 9,433,620 relates to pharmaceutical compositions of lurasidone or salts thereof with one or more water-insoluble pharmaceutical excipients. The invention also relates to processes for the preparation of such compositions and use thereof for treatment of schizophrenia, bipolar disorders or senile dementia.

U.S. Pat. No. 7,727,553 provides oral preparations with good disintegration containing a slightly water-soluble active ingredient, which comprise a mixture of a solid formed product (e.g. a granule) and a second disintegrant wherein said solid formed product comprises a slightly water-soluble active ingredient, a first disintegrant and a water-soluble excipient which is formed by using a water-soluble polymer binder, or comprises a solid formed product prepared from a slightly water-soluble active ingredient, a disintegrant and a sugar alcohol by using a water-soluble polymer binder.

Int. Res. J. Pharm. App. Sci., 2014; 4(1):78-87, Bhandari Neeraj et a. "A review on immediate release drug delivery system" discloses various techniques used in the preparation of immediate release tablets.

Asian Journal of Pharmaceutical Technology and Innovation, Vol 2, No 7 (2014), Ranjith Reddy Kondeti et at, "A Comparative Study on Different Methods of Granulation on Tablet Properties" discloses methods to evaluate the different process of granulation techniques for the preparation of tablets.

It is well known in the art that the active ingredient in a formulation represents a very small portion of the overall tablet and the challenge is to ensure that each tablet has the same amount of active ingredient. At times, merely blending the ingredients is not enough, the active ingredient may segregate from the other ingredients in the blending process. The ingredients may be incompatible because of particle size, particle density, flow characteristics, compressibility, and moisture content. These incompatibilities can cause problems such as segregation during blending or during transfer of the product to the press as well as separation of the active on the tablet press.

Granulating the active ingredient by itself and then blending it with the rest of the ingredients is one solution to the segregation problem. Different granulation techniques include Wet granulation, Dry granulation, Top spray granulation and Direct Compression. The various granulation techniques have different effect on the tablet properties such as hardness, friability, weight variation, disintegration time and in vitro dissolution.

Lurasidone has poor water solubility therefore, it is difficult to prepare a pharmaceutical preparation having equivalent dissolution profile, and even more challenging to have such equivalent in vitro (dissolution) profile over a wide range of medicament content in comparison with reference product viz. LATUDA®. There exists an absolute need for the development of an oral composition prepared by a technique which will enhance the drug release and improve the in vitro dissolution profile. Moreover, there is a need to provide a simpler and economically viable process of manufacturing, thus enabling overall cost effective production of lurasidone product.

In consideration of the need as indicated above, the inventors of present invention has carried out extensive research to evaluate the different process of granulation techniques for the preparation of oral formation comprising an active ingredient lurasidone or its pharmaceutically acceptable salt(s) or solvate(s) thereof and one or more pharmaceutical excipient(s) that can impact the in vitro drug release of the product. The method of granulation has been chosen based on the ingredient's individual characteristics and ability to flow, compress, eject, and disintegrate. The inventors of the present invention have thoroughly investigated each ingredient in the formula, the combination of ingredients, and how they work with each other and accordingly a proper granulation process has been devised and applied.

SUMMARY OF THE INVENTION

In one aspect, the present invention relates to an oral pharmaceutical composition comprising lurasidone or its pharmaceutically acceptable salt(s) or solvate(s) thereof and one or more pharmaceutical excipient(s).

In another aspect, there is provided an oral pharmaceutical composition comprising lurasidone or its pharmaceutically acceptable salt(s) or solvate(s) thereof, microcrystalline cellulose and one or more other pharmaceutical excipient(s).

In yet another aspect, there is provided an oral pharmaceutical composition comprising lurasidone or its pharmaceutically acceptable salt(s) or solvate(s) thereof, microcrystalline cellulose, one or more diluent(s), one or more binder(s), one or more disintegrant(s), one or more lubricant(s), optionally one or more glidant(s) and optionally coating material(s).

In another aspect, there is provided a process for the preparation of an oral pharmaceutical composition comprising lurasidone or its pharmaceutically acceptable salt(s) or solvate(s) thereof and one or more pharmaceutical excipient(s).

In another aspect, there is provided a process for the preparation of an oral pharmaceutical composition comprising lurasidone or its pharmaceutically acceptable salt(s) or solvate(s) thereof and one or more pharmaceutical excipient(s) wherein the composition is prepared by a granulation technique which has a significant impact on drug release.

In another aspect, there is provided a process for the preparation of an oral pharmaceutical composition comprising lurasidone or its pharmaceutically acceptable salt(s) or solvate(s) thereof and one or more pharmaceutical excipient(s) wherein the composition is prepared by top spray granulation technique.

In a further aspect, there is provided a process for the preparation of an oral pharmaceutical composition comprising lurasidone or its pharmaceutically acceptable salt(s) or solvate(s) thereof and one or more pharmaceutical excipient(s) which are granulated using 40% to 250% of granulating solution by top spray granulation process.

In another further aspect, there is provided a method for treating or preventing various conditions, diseases, disorders, comprising administering to a subject in need thereof any one of the compositions of the present invention in an amount effective to treat or prevent a condition, a disease or a disorder.

In another further aspect, there is provided use of an oral pharmaceutical composition comprising lurasidone or its pharmaceutically acceptable salt(s) or solvate(s) thereof and one or more pharmaceutical excipient(s), for the manufacture of a medicament for treating or preventing various conditions, diseases or disorders.

In a still further aspect, the present invention relates to a pharmaceutical kit comprising: (a) lurasidone or its pharmaceutically acceptable salt(s) or solvate(s) thereof and one or more pharmaceutical excipient(s); and (b) optionally a package insert comprising instructions for using the said pharmaceutical composition.

These and other aspects and advantages of the present invention will be apparent to those skilled in the art from the following description.

BRIEF DESCRIPTION OF DRAWINGS OF THE INVENTION

DETAILED DESCRIPTION OF THE INVENTION

Figure 1:
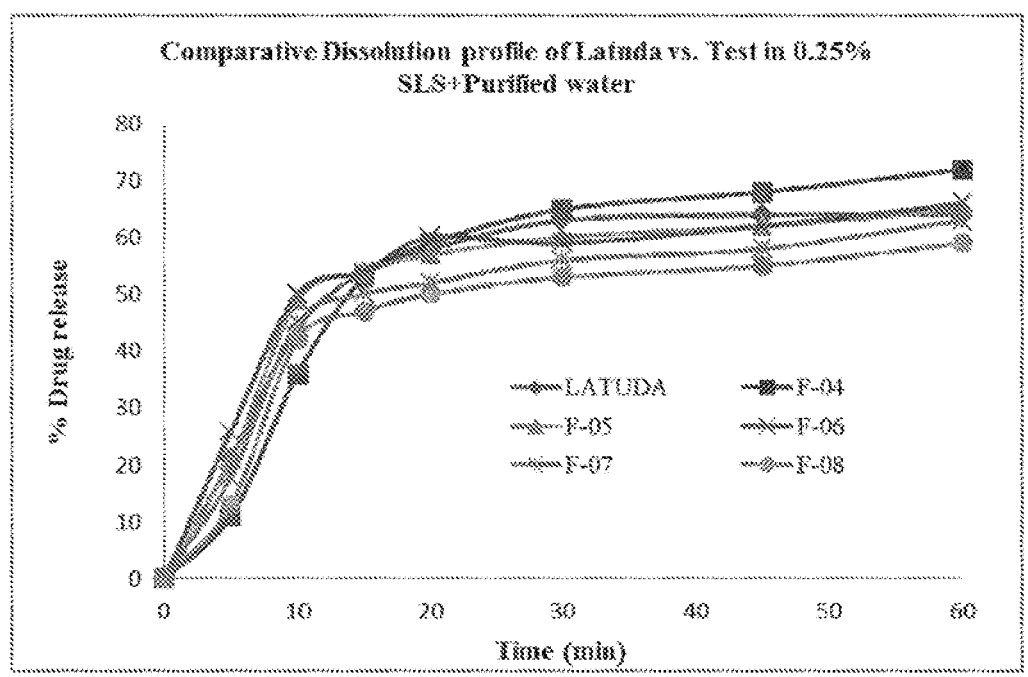
FIG. 1 represents release profile of different compositions of Lurasidone coated tablets shown in Table 4.
Figure 2:
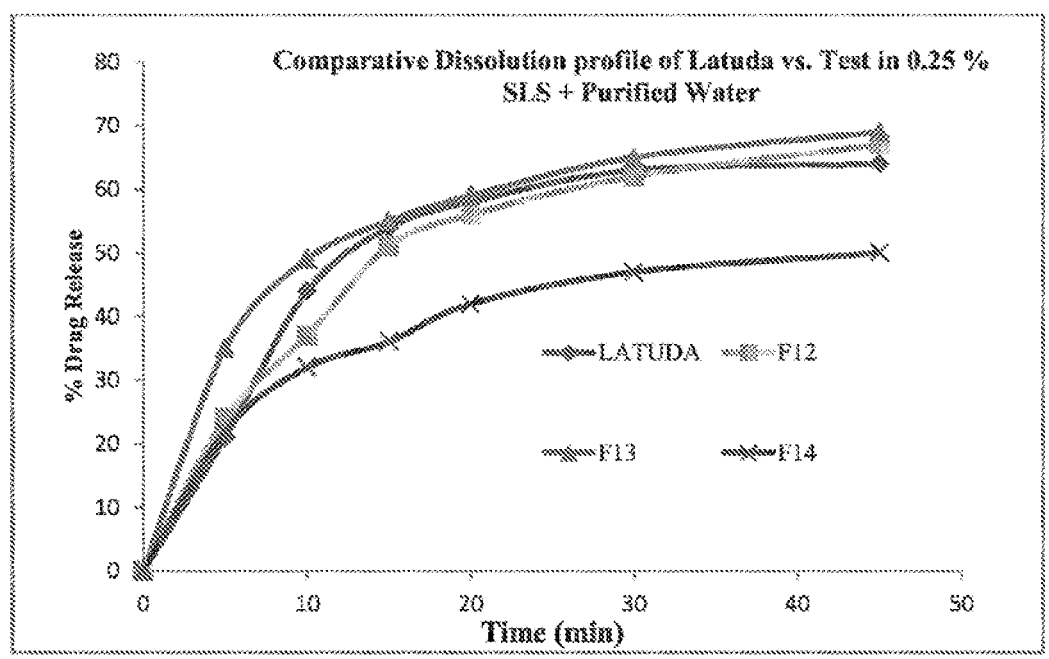
FIG. 2 represents release profile of Lurasidone compositions with different concentration of corn starch shown in Table 8.

It should be understood that the detailed description and specific examples, while indicating embodiments of the invention, are given by way of illustration only, since various changes and modifications within the spirit and scope of the invention will become apparent to those skilled in the art. One skilled in the art, based upon the definitions herein, may utilize the present invention to its fullest extent. The following specific embodiments are to be construed as merely illustrative, and not limitative of the remainder of the disclosure in any way whatsoever.

Except as defined herein, all the technical and scientific terms used herein have the same meaning as commonly understood by one of ordinary skill in the art to which the invention relates.

Definitions

For the purpose of the disclosure, listed below are definitions of various terms used to describe the present invention. Unless otherwise indicated, these definitions apply to the terms as they are used throughout the specification and the appended claims, either individually or as part of a larger group. They should not be interpreted in the literal sense. They are not general definitions and are relevant only for this application.

It should be noted that, as used in this specification and the appended claims, the singular forms "a," "an," and "the" include plural referents unless the content clearly dictates otherwise.

It should be noted that the term "or" is generally employed in its sense including "and/or" unless the content clearly dictates otherwise.

As used herein, the term "about" means approximately and in the context of numerical values the term "about" can be construed to estimate a value that is ±10% of the value or range recited.

The term "excipient(s)" as used herein means a diluent, binder, disintegrant, glidant, lubricant, coating material or the like, which is non-toxic, and inert, which does not have undesirable effects on a subject to whom it is administered and is suitable for delivering a therapeutically active agent (lurasidone) to the target site without affecting the therapeutic activity of the said agent.

The term "pharmaceutically acceptable salt(s)" means salt(s) of lurasidone, which can be prepared by treating lurasidone with an appropriate acid or a base. Examples of pharmaceutically acceptable acid addition salts include, but are not limited to, those derived from inorganic acids such as hydrochloric acid, nitric acid, phosphoric acid, sulfuric acid and the like, as well as the salts derived from organic acids such as acetic acid, trifluoroacetic acid, propionic acid, oxalic acid, maleic acid, benzoic acid, succinic acid, fumaric acid, phthalic acid, benzenesulfonic acid, p-toluenesulfonic acid, citric acid, tartaric acid, methanesulfonic acid and the like.

Examples of pharmaceutically acceptable base addition salts include, but are not limited to, sodium, potassium, calcium, magnesium, ammonium salts or an organic base salt. Examples of pharmaceutically acceptable organic base addition salts include, but are not limited to, those derived from organic bases such as lysine, arginine, guanidine, and the like.

As used herein, the term "formulation" or "composition" or "pharmaceutical composition" or "dosage form" as used herein synonymously include solid dosage forms such as granules, multiunit particulate systems (MUPS), pellets, spheres, tablets, capsules, mini-tablets, layered tablets, beads, particles and the like; and liquid dosage forms such as solutions, suspensions, emulsions, colloids and the like, meant for oral administration. The active pharmaceutical compound is lurasidone.

Within the context of the present invention and as used herein the term "lurasidone" unless indicated otherwise in the entire specification, refers to lurasidone in its free form, or as a pharmaceutically acceptable salt or solvate thereof.

Within the context of the present invention and as used herein, unless indicated otherwise, references to total weight of the pharmaceutical composition refers to the total weight of the active agent(s) and pharmaceutically acceptable excipient(s).

Within the context of the present invention and as used herein the term "subject" refers to an animal, preferably a mammal, and most preferably a human. In the context of the present invention, the term "mammal" is used interchangeably with the term "patient" or "subject". In the context of the present invention, the phrase "a subject in need thereof" means a subject (patient) in need of the treatment of a disease or disorder for which lurasidone is used.

Within the context of the present invention and as used herein the term 'diluent' refers to an agent used as filler in order to achieve the desired composition volume or weight. The diluent may be present in the pharmaceutical composition in the form of a single compound or in the form of a mixture of compounds. Diluents are often added to tablet formulations to provide better tablet properties such as to improve cohesion, to allow direct compression manufacturing, to enhance flow and to adjust weight of tablet as per die capacity. Diluents are generally classified into three categories namely organic, inorganic and co-processed diluents. The organic diluents include but are not limited to, lactose such as α-lactose monohydrate, spray dried lactose and anhydrous lactose, starch such as potato starch, corn starch or maize starch, and pregelatinized starch, sucrose, mannitol, sorbitol, cellulose such as powdered cellulose and microcrystalline cellulose. The inorganic diluents include but are not limited to calcium phosphates such as anhydrous dibasic calcium phosphate, dibasic calcium phosphate and tribasic calcium phosphate. Some of the insoluble diluents include but are not limited to starch, powdered cellulose, microcrystalline cellulose, calcium phosphate and the like. Some of the soluble diluents include but are not limited to lactose, sucrose, mannitol, sorbitol and the like.

Binders are dry powders or liquid which are added during granulation process to promote granules and cohesiveness. Binders are, but not limited to, cellulose and its derivatives including, ethyl cellulose, hydroxypropyl cellulose, hydroxypropyl methylcellulose (hypromellose), methylcellulose and hydroxyethyl cellulose, carboxymethyl cellulose, gelatin, liquid glucose, corn starch or maize starch, pregelatinized starch, hydrocolloids, sugars, polyvinyl pyrrolidone, sodium alginate, acacia, alginic acid, tragacanth, xanthan, used either alone or combinations thereof.

Disintegrant as used in herein refers to any material that facilitates the break-up of a tablet prepared from the composition when placed in contact with an aqueous medium. Suitable disintegrants include, but are not limited to, crospovidone, sodium starch glycolate, hydroxypropyl starch, microcrystalline cellulose, carboxymethylcellulose sodium or calcium, croscarmellose sodium, pregelatinized starch, polacrilin potassium, low-substituted hydroxypropylcellulose, sodium or calcium alginate, agar, guar gum, chitosan, alginic acid and mixtures thereof.

Glidants improve the flowability of the composition. Exemplary glidants are, but not limited to, fumed silica (colloidal silicon dioxide), colloidal silica, powdered cellulose, talc, tribasic calcium phosphate, magnesium stearate, magnesium carbonate, mixtures thereof and the like.

Lubricants are added in small quantities to tablet formulations to improve certain processing characteristics. The role of the lubricants is to ensure that tablet formation and ejection can occur with low friction between the tablet ingredients and the die walls of the tableting machine. Lubricant prevents sticking to punch faces and enhances product flow by reducing interparticulate friction. The lubricant may be present in the pharmaceutical composition in the form of a single compound or in the form of a mixture of compounds. Lubricants are, but not limited to sodium oleate, sodium stearate, sodium benzoate, sodium chloride, stearic acid, sodium stearyl fumarate, calcium stearate, magnesium stearate, magnesium lauryl sulfate, sodium stearyl fumarate, sucrose esters or fatty acid, zinc, polyethylene glycol, talc, mixtures thereof and the like.

One or more of these excipients can be selected and used by the artisan having regard to the particular desired properties of the solid dosage form. The amount of each type of excipient employed, e.g. diluent, binder, disintegrant, glidant and lubricant may vary within ranges conventional in the art.

Suitable pharmaceutical compositions include, but are not limited to, capsules, tablets, granules, powders and unit dose pockets. Preferably the oral pharmaceutical composition is a tablet. The tablet can be coated or non-coated.

Coating materials are, but not limited to, sugars, hydroxypropyl methylcellulose (hypromellose), hydroxypropyl cellulose, methylcellulose, ethylcellulose, polyvinyl alcohol, sodium carboxylmethylcellulose, coatings based on methacrylic acid and its esters, such as Eudragit®, mixtures thereof and the like. As alternatives for the above coating materials, sometimes pre-formulated coating products such as those sold as OPADRY™ will be used, for example Opadry White or Opadry Green. The products sold in a solid form require only mixing with a liquid before use. Alternatively, film-forming agents may be applied as powders, using suitable powder coating equipment known in the art.

Microcrystalline cellulose (MCC) is a purified, partially depolymerized cellulose prepared by treating alpha cellulose (type $I_\beta$), obtained as a pulp from fibrous plant material, with mineral acids. MCC is generally considered as the diluent having the best binding properties and is recognized as one of the preferred direct compression binders. In addition to its dry binding properties, and in comparison to brittle excipients. MCC is self-disintegrating with low lubricant requirement due to its extremely low coefficient of friction and its very low residual die wall pressure. MCC has other advantages including broad compatibility with APIs, physiological inertness, ease of handling, and security of supply (*International Journal of Pharmaceutics*; Volume 473, Issues 1-2, 1 Oct. 2014, Pages 64-72).

In one aspect, the present invention relates to an oral pharmaceutical composition comprising lurasidone or its pharmaceutically acceptable salt(s) or solvate(s) thereof with one or more pharmaceutical excipient(s).

In another aspect, the present invention relates to an oral pharmaceutical composition comprising lurasidone or its pharmaceutically acceptable salt(s) or solvate(s) thereof, microcrystalline cellulose and one or more other pharmaceutical excipient(s).

In an embodiment, the oral pharmaceutical composition comprises lurasidone or its pharmaceutically acceptable salt(s) or solvate(s) thereof, microcrystalline cellulose, one or more diluent(s), one or more binder(s), one or more disintegrant(s), one or more lubricant(s), optionally one or more glidant(s) and optionally coating material(s).

In an embodiment, the oral pharmaceutical composition comprises a pharmaceutically acceptable salt of lurasidone as lurasidone hydrochloride.

In an embodiment, the oral pharmaceutical composition contains lurasidone in the range of about 10% w/w to about 40% w/w of the composition.

In an embodiment, the oral pharmaceutical composition contains lurasidone in the range of about 15% w/w to about 30% w/w of the composition.

In an embodiment, the ratio of lurasidone to microcrystalline cellulose ranges from about 2:1 to about 10:1.

In a further embodiment, the ratio of lurasidone to microcrystalline cellulose is about 2:1 to about 6:1.

In a still further embodiment, the ratio of lurasidone to microcrystalline cellulose is about 2:1 to about 4:1.

In an embodiment, the pharmaceutically acceptable excipient(s) is selected from the group consisting of diluent, binder, disintegrant, lubricant, optionally glidant, optionally coating material or a combination thereof.

In an embodiment, the diluent is selected from the group consisting of lactose such as α-lactose monohydrate, spray dried lactose and anhydrous lactose, starch such as potato starch, corn starch or maize starch and pregelatinized starch, sucrose, mannitol, sorbitol, cellulose such as powdered cellulose and microcrystalline cellulose, calcium phosphates such as anhydrous dibasic calcium phosphate, dibasic calcium phosphate and tribasic calcium phosphate and the like. The diluent may be used in the range of about 55-85% by weight of the composition.

In an embodiment, the binder is selected from the group consisting of cellulose and its derivatives including, ethyl cellulose, hydroxypropyl cellulose, hydroxypropyl methylcellulose, methylcellulose and hydroxyethyl cellulose, carboxymethyl cellulose; gelatin, liquid glucose; corn starch or maize starch; pregelatinized starch; hydrocolloids; sugars; polyvinyl pyrrolidone, sodium alginate, acacia, alginic acid, tragacanth and xanthan, used either alone or combinations thereof. The binder may be used in the range of about 1-10% by weight of the composition.

In another embodiment, the disintegrant is selected from the group consisting of crospovidone, sodium starch glycolate, hydroxypropyl starch, microcrystalline cellulose, carboxymethylcellulose sodium or calcium, croscarmellose sodium, pregelatinized starch, polacrilin potassium, low-substituted hydroxypropylcellulose, sodium or calcium alginate, agar, guar gum, chitosan, alginic and the like used either alone or in combination thereof. The disintegrant may be used in the range of about 0.5-3% by weight of the composition.

In another embodiment, the glidant is selected from the group consisting of fumed silica (colloidal silicon dioxide), colloidal silica, powdered cellulose, talc, tribasic calcium phosphate, magnesium stearate, magnesium carbonate and the like used either alone or in combination thereof. The glidant may be used in the range of about 0.5-5% by weight of the composition.

In another embodiment, the lubricant is selected from the group consisting of sodium oleate, sodium stearate, sodium benzoate, sodium chloride, stearic acid, sodium stearyl fumarate, calcium stearate, magnesium stearate, magnesium lauryl sulfate, sodium stearyl fumarate, sucrose esters or fatty acid, zinc, polyethylene glycol, talc, mixtures thereof and the like used either alone or in combinations thereof. The lubricant may be used in the range of about 0.5-3% by weight of the composition.

In an embodiment, the diluent is selected from the group consisting of mannitol, starch and microcrystalline cellulose or a combination thereof.

In an embodiment, the diluent starch is selected from the group consisting of potato starch, corn starch or maize starch and pregelatinized starch.

In another embodiment, the diluent starch is in the range of about 3% w/w to about 20% w/w of the composition.

In an embodiment, the binder is hydroxypropyl methylcellulose.

In an embodiment, the disintegrant is croscarmellose sodium.

In an embodiment, the disintegrant is extragranular.

In an embodiment, the glidant is fumed silica.

In an embodiment, the glidant, fumed silica is used with an extragranular disintegrant.

In an embodiment, the lubricant is magnesium stearate.

In another embodiment, the pharmaceutical composition of the present invention comprises lurasidone, mannitol, pregelatinized starch, microcrystalline cellulose, hydroxypropyl methyl cellulose, croscarmellose sodium and magnesium stearate.

In yet another embodiment, the pharmaceutical composition of the present invention comprises lurasidone, mannitol, corn starch, microcrystalline cellulose, hydroxypropyl methyl cellulose, croscarmellose sodium, colloidal silicon dioxide and magnesium stearate.

In another embodiment, the composition of the invention can be in standard-release, immediate-release, rapid-onset, sustained-release or dual-release form.

In another embodiment, the composition of the invention is immediate-release form.

Process for the Preparation of Lurasidone Composition:

In an aspect, the present invention relates to a process for preparing a pharmaceutical composition containing a therapeutically effective amount of lurasidone or its pharmaceutically acceptable salts or solvates thereof comprising:

combining lurasidone or its pharmaceutically acceptable salts or solvates with one or more pharmaceutically acceptable excipient(s);

wherein lurasidone or its pharmaceutically acceptable salts or solvates and said pharmaceutically acceptable excipient(s) are combined by top spray granulation process.

Process A:

In an embodiment, top-spray granulation process comprises:
 (i) sifting lurasidone or its pharmaceutically acceptable salts or solvates with the diluents through ASTM (American Standard Test Sieve Series) 20 mesh to form a mixture;
 (ii) blending the dry mixture of step (i) in a blender
 (iii) preparing the granulating solution with the binder;
 (iv) granulating the mixture of step (ii) using the granulating solution prepared in step (iii);
 (v) drying the granulated mixture of step (iv);
 (vi) sifting the dried granules obtained in step (v) through ASTM 30 mesh;
 (vii) sizing of retained dried granules if any obtained in step (vi);
 (viii) sifting of disintegrant and lubricant through ASTM 30 mesh & through ASTM 60 mesh respectively;
 (ix) blending of sized granules obtained in step (vii) with disintegrant (except lubricant) in blender;
 (x) blending the mixture of step (ix) with lubricant in blender;
 (xi) compressing the lubricated blend of step (x) into a final tablet; and
 (xii) optionally coating the tablets with a suitable coating material.

Process B:

In an embodiment, top-spray granulation process comprises:
 (i) sifting lurasidone or its pharmaceutically acceptable salts or solvates with the diluents through ASTM (American Standard Test Sieve Series) 20 mesh to form a mixture;
 (ii) blending the dry mixture of step (i) in a blender;
 (iii) preparing the granulating solution with the binder;
 (iv) granulating the mixture of step (ii) using the granulating solution prepared in step (iii);
 (v) drying the granulated mixture of step (iv);
 (vi) sifting the dried granules obtained in step (v) through ASTM 30 mesh;
 (vii) sizing of retained dried granules if any obtained in step (vi);
 (viii) sifting of disintegrant, glidant and lubricant through ASTM 30 mesh & through ASTM 60 mesh respectively;
 (ix) blending of sized granules obtained in step (vii) with disintegrant (except glidant and lubricant) in blender;
 (x) blending the mixture of step (ix) with lubricant in blender;
 (xi) compressing the lubricated blend of step (x) with glidant to form the final tablet; and
 (xii) optionally coating the tablets with a suitable coating material.

In an embodiment, the sifter used for sifting the ingredients lurasidone, mannitol, starch, microcrystalline cellulose is vibrator sifter.

In another embodiment, the dry blend can be performed in a suitable mixer, such as a container blender, fluid bed dryer, drum blender, v-blender or a high shear mixer.

In an embodiment, the granulating process can be performed using fluidized bed processor, fluid bed top spray granulator or fluidized spray drying.

In an embodiment, the granulating process used is top spray granulation wherein the granulating solution is prepared by mixing purified water in the range of 40% to 250% with a binder.

In an embodiment, the granulating process used is top spray granulation wherein the granulating solution is prepared by mixing purified water in the range of 100% to 250% with a binder.

In an embodiment, the granulating process used is top spray granulation wherein the granulating solution is prepared by mixing purified water in the range of 150% to 250% with a binder.

In an embodiment, the amount of granulating solution used in the granulation of mixture of lurasidone or its pharmaceutically acceptable salts or solvates and pharmaceutically acceptable excipient(s) is in the range of 40% to 250%.

In an embodiment, the amount of granulating solution used in the granulation of mixture of lurasidone or its pharmaceutically acceptable salts or solvates and pharmaceutically acceptable excipient(s) is in the range of 100% to 250%.

In an embodiment, the amount of granulating solution used in the granulation of mixture of lurasidone or its pharmaceutically acceptable salts or solvates and pharmaceutically acceptable excipient(s) is in the range of 150% to 250%.

In an embodiment, the in vitro drug release of the composition depends upon the amount of microcrystalline cellulose, binder and the purified water used in the granulating solution.

In an embodiment, the in vitro drug release of the composition enhances when the ratio of lurasidone to microcrystalline cellulose is about 2:1 to about 4:1.

In an embodiment, the in vitro drug release of the composition enhances when the proportion of binder in the composition is reduced.

In an embodiment, the in vitro drug release of the composition enhances when the glidant is used with an extragranular disintegrant.

In an embodiment, tablet compression can be performed in a tablet press, and the optional coating process can be performed in a coating pan or fluid bed.

In another embodiment, the tablet formulations produced in the scope of the present invention can optionally be coated in order to provide various release characteristics for instance fast release, sustained release, slow release or they are coated with film coating.

The compositions of the present invention can be packed into suitable containers such as bottles, blisters or pouch. Further, the packages may optionally contain a desiccant or an antioxidant or oxygen absorbent or combinations thereof.

In an aspect, the present invention relates to use of the pharmaceutical composition comprising lurasidone as a therapeutic agent for treatment of schizophrenia or bipolar disorders, wherein the said composition is as described herein above in one or more embodiments of the present invention.

In another embodiment, the present invention relates to a method of treating schizophrenia or bipolar disorders, comprising administering to a subject in need thereof a therapeutically effective amount of the lurasidone composition; wherein the said composition is as described in one or more embodiments of the present invention as described herein above.

In another embodiment, the present invention relates to use of the composition of lurasidone, for the manufacture of a medicament for treating schizophrenia or bipolar disorders; wherein the said composition is as described herein above in one or more embodiments of the present invention.

In another embodiment, the composition of lurasidone may be packaged in a suitable container depending upon the formulation and the method of administration of the composition. Suitable containers known to a person skilled in the art include blister pack or bottle pack.

In another embodiment, the present invention provides a pharmaceutical kit comprising lurasidone or its pharmaceutically acceptable salt(s) or solvate(s) thereof; and one or more pharmaceutically acceptable excipient(s). The kit may further comprise a package insert, including information about the indication, usage, doses, direction for administration, contraindications, precautions and warnings.

In another embodiment, the pharmaceutical compositions of the present invention can include all the dosage forms known to a person skilled in art, viz, formulations such as single unit dosage forms in the form of tablets, bilayer tablets, inlaid tablets, tablet in tablet, multilayered tablets, minitablets filled in capsules and the like; beads, pellets presented in a sachet, capsule or tablet capsules such as soft and hard gelatin; lozenges or sachets; granulates, microparticles, multiparticulates, powder and the like.

It is understood that modifications that do not substantially affect the activity of the various embodiments of this invention are included within scope of the invention disclosed herein. Accordingly, the following examples are intended to illustrate but not to limit the scope of the present invention.

EXAMPLES

TABLE 1

Composition or Lurasidone tablets (40 mg):
(Conditions: Absence of microcrystalline cellulose and % of water used in granulating solution is between 40-80%)

| Ingredients | Quantity (% w/w) | | |
|---|---|---|---|
| Batch No. | F-01 | F-02 | F-03 |
| Intragranular | | | |
| Lurasidone HCl | 25 | 25 | 25 |
| Mannitol | 52 | 54.5 | 53 |
| Pregelatinized starch | 15 | 15 | 15 |
| Hydroxypropyl methylcellulose | 3 | 3 | 4.5 |
| Croscarmellose sodium | 2 | 0.75 | 0.75 |
| Purified water | 40% | 60% | 80% |
| Extragranular | | | |
| Croscarmellose sodium | 2 | 0.75 | 0.75 |
| Magnesium stearate | 1 | 1 | 1 |
| Total | 100 | 100 | 100 |

TABLE 2

In-vitro drug release (%) of F-01 to F-03 batches Lurasidone test tablet is released in 0.25% Sodium Lauryl Sulphate (SLS) + Purified Water environment, under conditions of 900 mL of a dissolution medium at 37° C. ± 0.5° C., USP method-II (paddle), 50 rpm (revolution per minute) speed wherein the tablet exhibits a dissolution profile as follows:

| Time (Min) | LATUDA® (40 mg) (% Mean) | F-01 (% Mean) | F-02 (% Mean) | F-03 (% Mean) |
|---|---|---|---|---|
| 5 | 21 | 21 | 20 | 9 |
| 10 | 44 | 36 | 30 | 35 |

TABLE 2-continued

In-vitro drug release (%) of F-01 to F-03 batches Lurasidone test tablet is released in 0.25% Sodium Lauryl Sulphate (SLS) + Purified Water environment, under conditions of 900 mL of a dissolution medium at 37° C. ± 0.5° C., USP method-II (paddle), 50 rpm (revolution per minute) speed wherein the tablet exhibits a dissolution profile as follows:

| Time (Min) | LATUDA® (40 mg) (% Mean) | F-01 (% Mean) | F-02 (% Mean) | F-03 (% Mean) |
|---|---|---|---|---|
| 15 | 54 | 41 | 35 | 43 |
| 20 | 58 | 44 | 39 | 47 |
| 30 | 63 | 48 | 41 | 51 |
| 45 | 64 | 50 | 44 | 54 |
| 60 | 64 | 53 | 48 | 58 |
| F2 (Similarity factor) | — | 41.77 | 33.63 | 46.14 |

Results:

From the above table, it can be found that at initial time point of 5 min, % drug release is slower than LATUDA® due to absence of microcrystalline cellulose and low % of water used in granulating solution. From the similarity factor F2 (F2<50) it was also observed that, the compositions F-01 to F-03 are not similar to LATUDA®.

TABLE 3

Composition of Lurasidone tablets (40 mg):
(Conditions: Presence of microcrystalline cellulose in different proportions and % of water used in granulating solution is between 100-160%)

| Ingredients | Quantity (% w/w) | | | | |
|---|---|---|---|---|---|
| Batch No. | F-04 | F-05 | F-06 | F-07 | F-08 |
| Intra-granular | | | | | |
| Lurasidone HCl | 25 | 25 | 25 | 25 | 25 |
| Mannitol | 47.5 | 45 | 42.5 | 45 | 45 |
| Pregelatinized starch | 15 | 15 | 15 | 15 | 15 |
| Microcrystalline cellulose | 5 | 7.5 | 10 | 7.5 | 7.5 |
| Hydroxypropy methylcellulose | 5 | 5 | 5 | 5 | 5 |
| Croscarmellose sodium | 0.75 | 0.75 | 0.75 | 0.75 | 0,75 |
| Purified water | 160% | 160% | 160% | 125% | 100% |
| Extra-granular | | | | | |
| Croscarmellose sodium | 0.75 | 0.75 | 0.75 | 0.75 | 0,75 |
| Magnesium stearate | 1 | 1 | 1 | 1 | 1 |
| Total | 100 | 100 | 100 | 100 | 100 |

TABLE 4

In-vitro drug release of F-04 to F-08 batches Lurasidone test tablet is released in 0.25% SLS + Purified Water environment, under conditions of 900 mL of a dissolution medium at 37° C. ± 0.5° C., USP method-II (paddle), 50 rpm (revolution per minute) speed wherein the tablet exhibits a dissolution profile as follows:

| Time (Min) | LATUDA® % Mean | F-04 % Mean | F-05 % Mean | F-06 % Mean | F-07 % Mean | F-08 % Mean |
|---|---|---|---|---|---|---|
| 5 | 21 | 11 | 21 | 26 | 18 | 13 |
| 10 | 44 | 36 | 49 | 50 | 45 | 42 |
| 15 | 54 | 53 | 54 | 54 | 50 | 47 |

TABLE 4-continued

In-vitro drug release of F-04 to F-08 batches
Lurasidone test tablet is released in 0.25% SLS + Purified Water
environment, under conditions of 900 mL of a dissolution medium
at 37° C. ± 0.5° C., USP method-II (paddle), 50 rpm (revolution
per minute) speed wherein the tablet exhibits a
dissolution profile as follows:

| Time (Min) | LATUDA ® % Mean | F-04 % Mean | F-05 % Mean | F-06 % Mean | F-07 % Mean | F-08 % Mean |
|---|---|---|---|---|---|---|
| 20 | 58 | 59 | 57 | 60 | 52 | 50 |
| 30 | 63 | 65 | 60 | 59 | 56 | 53 |
| 45 | 64 | 68 | 62 | 62 | 58 | 55 |
| 60 | 64 | 72 | 65 | 66 | 63 | 59 |
| F2 | — | 66.20 | 74.21 | 69.90 | 61.24 | 53.05 |

Results:

From the above table, it can be seen that use of microcrystalline cellulose in the composition has enhanced the initial dispersion at 5 min time point. It is also found that the dissolution of the compositions F-04 to F-08 in comparison with reference product Latuda has increased with increase in % of water in granulation. Thus, F2 value increases when the % of water used in the granulating solution increases. The F2 value of batch F-05 is the highest.

TABLE 5

Composition of Lurasidone tablets:
(Conditions: Presence of microcrystalline cellulose in similar
proportions, difference in proportions of binder and % at
water used in granulating solution is between 160-200%)

| Ingredients | Quantity (% w/w) | | |
|---|---|---|---|
| Batch No. | F-09 | F-10 | F-11 |
| Intra-granular | | | |
| Lurasidone HCl | 25 | 25 | 25 |
| Mannitol | 45.5 | 46 | 45.5 |
| Pregelatinized starch | 15 | 15 | 15 |
| Microcrystalline cellulose | 7.5 | 7.5 | 7.5 |
| Hydroxypropyl methylcellulose | 4.5 | 4.0 | 4.5 |
| Croscarmellose sodium | 0.75 | 0.75 | 0.75 |
| Purified water | 160% | 160% | 200% |
| Extra-granular | | | |
| Croscarmellose sodium | 0.75 | 0.75 | 0.75 |
| Magnesium stearate | 1 | 1 | 1 |
| Total | 100 | 100 | 100 |

TABLE 6

In-vitro drug release of F-09 to F-11 batches
Lurasidone test tablet is released in 0.25% SLS + Purified Water
environment, under conditions of 900 mL of a dissolution
medium at 37° C. ± 0.5° C., USP method-II (paddle), 50 rpm
(revolution per minute) speed wherein the tablet exhibits a
dissolution profile as follows:

| Time (Min) | LATUDA ® % Mean | F-09 % Mean | F-10 % Mean | F-11 % Mean |
|---|---|---|---|---|
| 5 | 21 | 13 | 22 | 37 |
| 10 | 44 | 39 | 48 | 52 |
| 15 | 54 | 51 | 57 | 57 |
| 20 | 58 | 56 | 58 | 59 |
| 30 | 63 | 59 | 62 | 60 |
| 45 | 64 | 61 | 64 | 61 |
| 60 | 64 | 63 | 69 | 68 |
| F2 | — | 69.40 | 78.12 | 65.49 |

Results:

From the above table, it can be seen that use of microcrystalline cellulose in the composition with reduced binder content has enhanced the initial dispersion at 5 min time point. It is also found that the F2 value depends on the % of water used in the granulating solution. The F2 value of hatch F-10 is the highest.

TABLE 7

Composition of Lurasidone tablets (40 mg):
(Conditions: Constant proportion of microcrystalline cellulose
and binder, difference in proportion of corn starch used in
range of 5 to 15%)

| Ingredients | Quantity (% w/w) | | |
|---|---|---|---|
| BatchNo. | F-12 | F-13 | F-14 |
| Intra-granular | | | |
| Lurasidone HCl | 25 | 25 | 25 |
| Mannitol | 51.5 | 47.5 | 43.5 |
| Maize starch/Corn starch | 5 | 11 | 15 |
| Microcrystalline cellulose | 7.5 | 7.5 | 7.5 |
| Hypromellose | 4.5 | 4.5 | 4.5 |
| Purified water | 200% | 200% | 200% |
| Extra-granular | | | |
| Croscarmellose sodium | 1.5 | 1,5 | 1,5 |
| Colloidal silicon dioxide | 2 | 2 | 2 |
| Magnesium stearate | 1 | 1 | 1 |
| Total | 100 | 100 | 100 |

TABLE 8

In-vitro drug release (%) of F-12 to F-14 batches
Lurasidone test tablet is released in 0.25% SLS + Purified Water
environment, under conditions of 900 mL of a dissolution
medium at 37° C. ± 0.5° C., USP method-II (paddle), 50 rpm
(revolution per minute) speed wherein the tablet exhibits a
dissolution profile as follows:

| Time (Min) | LATUDA ® (40 mg) % Mean | F-12 % Mean | F-13 % Mean | F-14 % Mean |
|---|---|---|---|---|
| 5 | 21 | 24 | 35 | 22 |
| 10 | 44 | 37 | 49 | 32 |
| 15 | 54 | 51 | 55 | 36 |
| 20 | 58 | 56 | 59 | 42 |
| 30 | 63 | 62 | 65 | 47 |
| 45 | 64 | 67 | 69 | 50 |

TABLE 8-continued

In-vitro drug release (%) of F-12 to F-14 batches
Lurasidone test tablet is released in 0.25% SLS + Purified Water
environment, under conditions of 900 mL of a dissolution
medium at 37° C. ± 0.5° C., USP method-II (paddle), 50 rpm
(revolution per minute) speed wherein the tablet exhibits a
dissolution profile as follows:

| Time (Min) | LATUDA ® (40 mg) % Mean | F-12 % Mean | F-13 % Mean | F-14 % Mean |
|---|---|---|---|---|
| 60 | 64 | 72 | 77 | 57 |
| F2 | — | 67 | 55 | 44 |

Results:

From the above table, it can be seen that the test performed with various level of corn starch from 5.00% to 15.00% w/w in drug product exhibited comparable dissolution profile with the reference product, LATUDA®.

We claim:

1. An oral pharmaceutical composition comprising:
   (a) lurasidone or its pharmaceutically acceptable salt(s) or solvates) thereof,
   (b) microcrystalline cellulose,
   (c) corn starch or maize starch; and
   (d) one or more other pharmaceutical excipient(s);
   wherein the ratio of lurasidone to microcrystalline cellulose is in the range from about 3:1 to about 4:1;
   wherein the corn starch or maize starch is in the range of about 3% w/w to about 11% w/w of the composition; and
      wherein the composition is prepared by granulating lurasidone or its pharmaceutically acceptable salt(s) or solvate(s) thereof, microcrystalline cellulose and, one or more other pharmaceutical excipient(s) using 100% to 250% of granulating solution.

2. The oral pharmaceutical composition as claimed in claim 1, comprising:
   (a) lurasidone or its pharmaceutically acceptable salt(s) or solvate(s) thereof,
   (b) microcrystalline cellulose,
   (c) corn starch or maize starch,
   (d) one or more diluent(s),
   (e) one or more binder(s),
   (f) one or more disintegrant(s),
   (g) one or more lubricant(s),
   (h) optionally one or more glidant(s), and
   (i) optionally coating material(s);
   wherein the ratio of lurasidone to microcrystalline cellulose is in the range from about 3:1 to about 4:1.

3. The oral pharmaceutical composition as claimed in claim 1, wherein the pharmaceutical acceptable salt of lurasidone is lurasidone hydrochloride.

4. The oral pharmaceutical composition as claimed in claim 1, wherein the pharmaceutically acceptable excipient(s) is selected from the group consisting of diluent, binder, disintegrant, lubricant, optionally glidant, optionally coating material or a combination thereof.

5. The oral pharmaceutical composition as claimed in claim 2, wherein the diluent is selected from the group consisting of α-lactose monohydrate, spray dried lactose and anhydrous lactose, corn starch or maize starch, sucrose, mannitol, sorbitol, powdered cellulose, microcrystalline cellulose, anhydrous dibasic calcium phosphate, dibasic calcium phosphate and tribasic calcium phosphate; or a mixture thereof.

6. The oral pharmaceutical composition as claimed in claim 5, wherein the diluent is selected from the group consisting of mannitol, corn starch or maize starch and microcrystalline cellulose or a combination thereof.

7. The oral pharmaceutical composition as claimed in claim 2, wherein the binder is selected from the group consisting of cellulose and its derivatives including, ethyl cellulose, hydroxypropyl cellulose, hydroxypropyl methylcellulose, methylcellulose and hydroxyethyl cellulose, carboxymethyl cellulose; gelatin, liquid glucose; corn starch or maize starch; hydrocolloids; sugars; polyvinyl pyrrolidone, sodium alginate, acacia, alginic acid, tragacanth and xanthan.

8. The oral pharmaceutical composition as claimed in claim 2, wherein the disintegrant is selected from the group consisting of crospovidone, sodium starch glycolate, hydroxypropyl starch, microcrystalline cellulose, carboxymethylcellulose sodium or calcium, croscarmellose sodium, polacrilin potassium, low-substituted hydroxypropylcellulose, sodium or calcium alginate, agar, guar gum, chitosan, and alginic.

9. The oral pharmaceutical composition as claimed in claim 8, wherein the disintegrant is used extragranularly.

10. The oral pharmaceutical composition as claimed in claim 2, Wherein the lubricant is selected from the group consisting of sodium oleate, sodium stearate, sodium benzoate, sodium chloride, stearic acid, sodium stearyl fumarate, calcium stearate, magnesium stearate, magnesium lauryl sulfate, sodium stearyl fumarate, sucrose esters or fatty acid, zinc, polyethylene glycol and talc.

11. The oral pharmaceutical composition as claimed in claim 2, Wherein the glidant is selected from the group consisting of fumed silica (colloidal silicon dioxide), colloidal silica, powdered cellulose, talc, tribasic calcium phosphate, magnesium stearate and magnesium carbonate.

12. The oral pharmaceutical composition as claimed in claim 10, wherein the glidant is fumed silica.

13. The oral pharmaceutical composition as claimed in claim 12, wherein the glidant, fumed silica is used with an extragranular disintegrant.

14. A process for preparing an oral pharmaceutical composition containing a therapeutically effective amount of lurasidone or its pharmaceutically acceptable salts or solvates thereof comprising: combining lurasidone or its pharmaceutically acceptable salts or solvates with one or more pharmaceutically acceptable excipient(s) wherein; lurasidone or its pharmaceutically acceptable salts or solvates and said pharmaceutically acceptable excipient(s) are granulated using 40% to 250% of granulating solution by top spray granulation process.

15. A method of treating schizophrenia or bipolar disorders, comprising administering to a subject in need thereof a therapeutically effective amount of lurasidone oral pharmaceutical composition as claimed in claim 1.

* * * * *

UNITED STATES PATENT AND TRADEMARK OFFICE
CERTIFICATE OF CORRECTION

Page 1 of 1

PATENT NO. : 11,260,055 B2
APPLICATION NO. : 16/476385
DATED : March 1, 2022
INVENTOR(S) : Shah et al.

It is certified that error appears in the above-identified patent and that said Letters Patent is hereby corrected as shown below:

On the Title Page

Item (73) Assignee:
Should read:
PIRAMAL PHARMA LIMITED

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*